(12) United States Patent
Verheijen

(10) Patent No.: US 6,239,875 B1
(45) Date of Patent: May 29, 2001

(54) PHOTOMETRIC MEASURING SYSTEM AND A HOLDER FOR SUCH A SYSTEM

(75) Inventor: Johan Hendrikus Verheijen, Berkel en Rodenrijs (NL)

(73) Assignee: Nederlandse Organisatie Voor Toegepast-Natuurwetenschappelijk, Delft (NL)

( * ) Notice: Subject to any disclaimer, the term of this patent is extended or adjusted under 35 U.S.C. 154(b) by 0 days.

(21) Appl. No.: 09/068,747

(22) PCT Filed: Nov. 18, 1996

(86) PCT No.: PCT/NL96/00456

§ 371 Date: May 13, 1999

§ 102(e) Date: May 13, 1999

(87) PCT Pub. No.: WO97/19339

PCT Pub. Date: May 29, 1997

(30) Foreign Application Priority Data

Nov. 17, 1995 (EP) .................................................. 95203146

(51) Int. Cl.[7] ............................ G01N 21/00; G01N 21/47
(52) U.S. Cl. ............................ 356/436; 356/440; 356/246
(58) Field of Search .................................... 356/440, 436, 356/244, 246; 250/373, 372

(56) References Cited

U.S. PATENT DOCUMENTS 4,004,150 * 1/1977 Natelson .............................. 250/373
4,498,780 * 2/1985 Banno et al. ..

FOREIGN PATENT DOCUMENTS

| 21 16 381 | * | 10/1972 | (DE) . |
| 40 21 855 A1 | * | 1/1992 | (DE) . |
| 0 046 430 A1 | * | 2/1982 | (EP) . |
| 0 545 284 A1 | * | 6/1993 | (EP) . |
| WO 93/20612 | * | 10/1993 | (WO) . |

* cited by examiner

Primary Examiner—Frank G. Font
Assistant Examiner—Amanda Merlino
(74) Attorney, Agent, or Firm—Hoffmann & Baron, LLP

(57) ABSTRACT

A photometric measuring system comprising a holder (2) provided with at least one liquid storage chamber (4) having an open upper end (10) for holding liquid (12) to be measured; at least one light generator (6) for generating an incoming light beam (8) towards the liquid storage chamber, so that at least a portion of the incoming light beam (8) enters the liquid storage chamber (4) though the open upper end (10); and at least one light detector (14) for detecting, during operation, at least a portion of the light (22) which has interacted with the liquid present in the liquid storage chamber (4), wherein, at least a portion of the inner walls of the storage chamber has been provided with a reflective surface (20), so that at least a portion of the light which has entered the storage chamber to interact with the liquid in the storage chamber will be reflected towards the open upper end and will leave the storage chamber through the open upper end; and wherein the light detector detects at least a portion of said light which has left the storage chamber through the open upper end.

8 Claims, 4 Drawing Sheets

PHOTOMETRIC MEASURING SYSTEM AND A HOLDER FOR SUCH A SYSTEM

The invention relates to a photometric measuring system, comprising a holder provided with at least one storage chamber for holding a fluid to be measured, at least one light generator for generating a light beam to interact with the fluid in the storage chamber and at least one light detector for detecting, during operation, at least a portion of the light which has interacted with the fluid present in the storage chamber, in which system at least a portion of the inner walls of the storage chamber has been provided with a reflective surface so that at least a portion of the light which has entered the storage chamber will be reflected and detected by the detector.

Such a photometric measuring system is known from DE-OS-2116381. In this document an absorption measuring apparatus for gases is described, wherein a gas is supplied into a storage chamber via porous walls and the storage chamber is closed by a light generator for generating a light beam to interact with the gas in the storage chamber and a detector for detecting a portion of said light beam, reflected by a reflective surface, located on the inner wall of the storage chamber opposite to the generator and the detector. This apparatus is not appropriate to be used for a liquid. Further there is permanent connection between storage chamber, generator and detector, with the consequence that the application of the measuring system is rather limited.

More appropriate photometric measuring systems are known and are used for performing photometric measurements on liquids, particularly on translucent liquids. More specifically this invention relates to a modified way of providing light to a sample and detecting its attenuation in the sample using a photometric measuring system employing a set of storage chambers arranged in a fixed matrix. Such storage chambers are also known as 'cuvettes'.

Photometric devices employing a set of cuvettes arranged in a fixed matrix are widespread. A generally used matrix arrangement is a microplate with a standard array of 8×12 wells made of an optically transparent material containing the liquid samples to be measured. such microtiter plates are very cheap and can be disposed of after use. Light passes vertically through the wells and its attenuation is detected with a suitable detector. a variety of systems based on these principles is in use. Variations include the number of light detectors, with at one extreme, a single detector and light beam and a mechanism to move the plate such, that each well subsequently is placed in the beam, or alternatively, a fixed plate can be employed and the beam can be moved in a stepwise or continuous fashion from well to well. Another extreme is that each well is placed in a separate beam and has a separate detector, thus allowing truly simultaneous measurements in all wells. Intermediate arrangements are employed where a group of wells, in most cases a row of 8 or 12 wells, are processed simultaneously by 8 or 12 beams and detectors.

Typically such devices consist of a light source, a monochromator to select the desired wavelength of light, an optical system and a detector with associated electronics. Furthermore an often automated system to move the plate and/or beam detector arrangement to enable measurement of all wells separately, can be present.

Devices like these are often employed in the enzymelinked immuno sorbent assay (ELISA) technique. This technique is widely used to detect and/or quantify a large variety of substances in, e.g., academic research, clinical chemistry, environmental chemistry, biotechnology or biochemistry.

Other applications are the measurement of enzyme reactions resulting in the conversion of a substrate into products with different spectral properties. Widely used are chromogenic peptide substrates for the detection of various proteases. Other applications are measurements of inorganic or organic compounds or the detection of particular reaction products of chemical reactions based on their spectral properties.

Due to the arrangement of the well between the light generator and the light detector, the light has to pass the microtiter plate and the range of wavelengths that can be employed is limited by the optical properties of the plate material. Frequently these disposable low cost microtiter plates are made from a transparant polymer, generally polystyrene, limiting their use to wavelengths between about 330–800 nm. Special polymer materials can extend this range to the near ultraviolet from 250 nm onwards. For wavelengths below this wavelength non-disposable microtiter plates with quartz windows exist, such plates are extremely expensive, fragile and not intended for single use and disposal such as is the case with the polymer plates.

The object of the present invention is to provide a photometric measuring system, which provides a solution for the above-referred to problem. Therefore, the photometric measuring system, according to the invention, is characterized in that, the holder is provided with a plurality of storage chambers and that in order to realise a photometric measurement which can be carried out with respect to a liquid in the storage chamber independent of the wavelength of the generated light beam, each storage chamber has an upper open end and the generator as well as the detector can be arranged at a predetermined distance above said upper open end, such that the light in the lightpath between the light generator and the detector does not meet any physical window.

Hence, in accordance with the present invention the light to be measured does not have to pass the material of the holder. Therefore, the storage chamber, according to the invention, can be made from low cost material, such as for example, polystyrene or polyethene. In accordance with the present invention the incoming light beam enters a storage chamber through its open end, interferes with the liquid present in the storage chamber, reflects on the reflecting surface back to the open end and subsequently leaves the storage chamber so that it can be detected by the light detector.

The invention will be further elucidated with reference to the drawings which should be interpreted as illustrative and not limiting the present invention. In the drawings.

Figure 2:
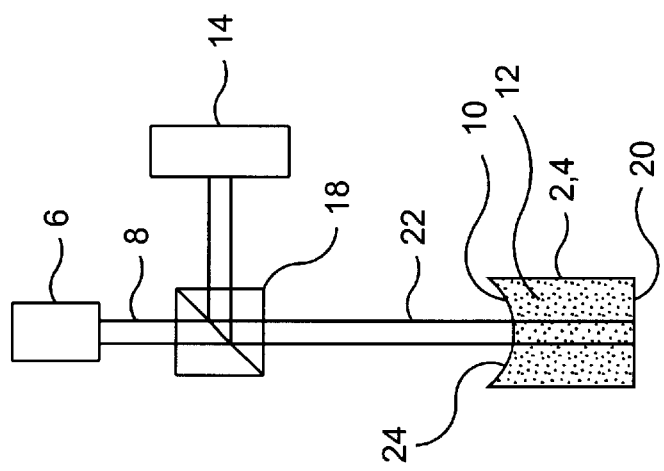
FIG. 2 shows a first embodiment of a photometric measuring system according to the invention.
Figure 1:
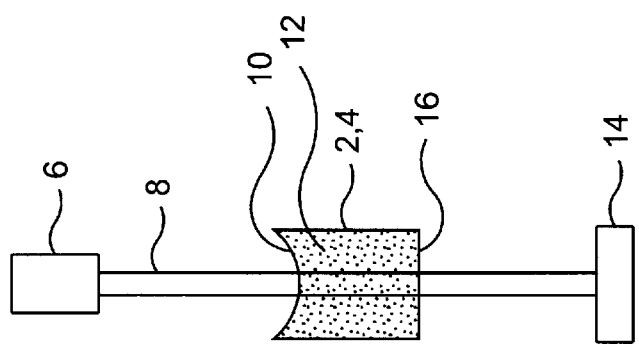
FIG. 1 shows an embodiment of a known photometric measuring system.

FIG. 1 with reference numeral 1, denotes a generally known photometric measuring system for measuring a liquid. In relation with the invention the phrase 'liquid' also includes suspensions and dispersions. The system 1 comprises a holder 2 provided with a liquid storage chamber 4. In fact according to this embodiment the holder and the liquid storage chamber are one and the same device. Furthermore, the system is provided with a light generator 6 for generating an incoming light beam 8 towards the liquid storage chamber 4. The incoming light beam 8 enters the liquid storage chamber 4 through an open end 10 of the liquid storage chamber 4. The liquid 12 to be measured is present in the liquid storage chamber 4. Furthermore, the system is provided with a light detector 14, which is positioned below the liquid storage chamber 4. The liquid storage chamber 4 is provided with a light transparent bottom 16. Consequently, the light beam 8 will interact with the liquid 12 and subsequently leave the storage chamber through the transparent bottom 16. The light detector 14 will therefore detect the light beam 8. Due to the attenuation of the light in the translucent liquid, information can be obtained about the liquid on the basis of the detected light beam. In case it is desired that the wavelength to be employed, can extend in a range, which is near to ultraviolet it is necessary that the bottom of the liquid storage chamber 4 is made from very special materials such as quartz. Such materials are, however, extremely expensive, fragile and not intended for single use and disposal. The invention provides a solution for these problems, wherein relatively cheap liquid storage chambers may be used without adversely effecting the quality of the measurement. Moreover the present invention provides additional advantages by which the quality of the measurement will be improved significantly relative to the known systems. A possible embodiment of the invention is shown in FIG. 2. All the figures features, which correspond with each other have been denoted by the same reference numeral. In the present invention the light beam 8, generated by the light generator 6, passes through a beam splitter 18 and subsequently enters the liquid storage chamber through the open upper end 10 of the chamber. The liquid storage chamber 4 is provided with a bottom 20 having a reflective surface. Therefore, the incoming light beam 8 is reflected back, such that a reflected outgoing light beam 22 is formed. The outgoing light beam 22 travels through the liquid 12 and leaves the liquid storage chamber 4 through its open upper end 10. The outgoing light beam 22 travels subsequently towards the beam splitter 18, where the outgoing beam 22 is reflected over an angle of 90° towards the light detector 14. Due to this special arrangement the system operates without any physical window in the light path between the incoming light beam, liquid and outgoing light beam. Hence, it is no longer necessary to provide the liquid storage chamber with a very expensive transparent bottom 16 if it is required that the wavelength of the light is close to the ultraviolet spectrum. Instead the bottom of the liquid storage chamber 4 should have a reflective surface. A reflective surface can be obtained with very cheap and well-known materials. Preferably, the incoming and outgoing light beams are directed vertically. This ensures that the incoming and outgoing light beams hit the liquid surface 24 in a direction which is perpendicular to this surface. Hence, the incoming and outgoing light beams will not be refracted at the transition from the liquid to the air and visa versa.

A major advantage of the present invention arises from its very concept that the light beam has to pass twice through the liquid present in the liquid storage chamber, thus increasing the length of the light path and by consequence increasing the light attenuation as compared with a conventional device in which the light passes the liquid only once. This leads to a higher sensitivity and lower detection limit with the same sample volume.

Figure 3:
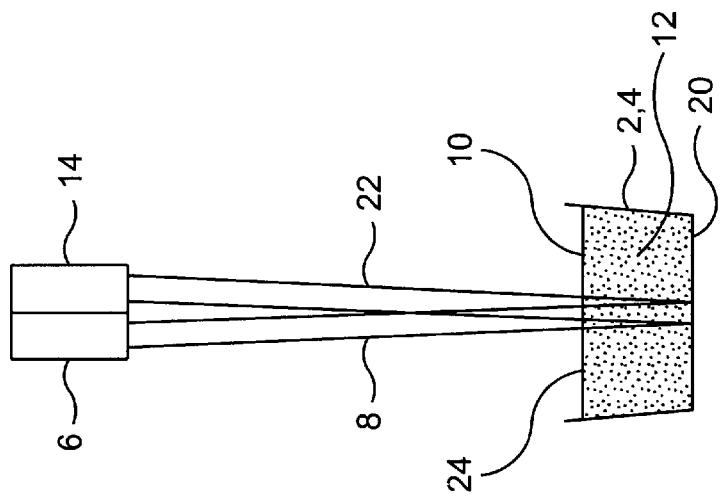
FIG. 3 shows a second embodiment of a photometric measuring system according to the invention.

FIG. 3 shows an embodiment, wherein the use of a beam splitter 18 is no longer necessary. In FIG. 3 the light generator 6 and the light detector 14 are positioned adjacent to each other. The incoming light beam 8 is transmitted towards the liquid storage chamber 4 having an angle relative to the reflector's surface 20 of the liquid storage chamber which is almost but not exactly 90°. This means that the outgoing light beam 22 is angled to the incoming light beam 8. The angle between the incoming light beam 8 and the outgoing light beam 22 is such that the outgoing light beam 22 falls on the light detector 14. The advantage of the system according to FIG. 3 is that it is not necessary to use a beam splitter 18. Thereby the quality of the measurement is further improved relative to the known systems. However, because of the fact that the incoming light beam 8 and the outgoing light beam 22 are not exactly perpendicular to the liquid surface 24, the incoming and outgoing light beams will be refracted slightly at the transition interface between the liquid and the open air above the liquid. In case that the angle on which the incoming and outgoing light beams are bent away varies, it is possible to adjust the distance between the light generator 6 and/or the light detector 14 on the one hand and the liquid storage chamber 4 on the other hand, such that the outgoing light beam 22 falls on the light detector 14. In FIG. 3 arrow P shows the direction in which the light detector 14 and/or the light generator 6 may be moved to obtain such an adjustment.

Figure 4A:
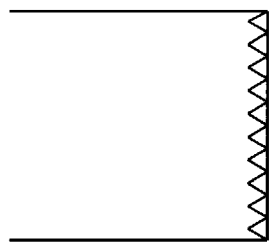
FIGS. 4a–4d show possible embodiments of a storage chamber of a system according to FIGS. 2, 3 and 5–7.
Figure 4B:
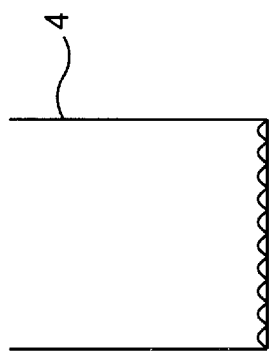
Figure 4C:
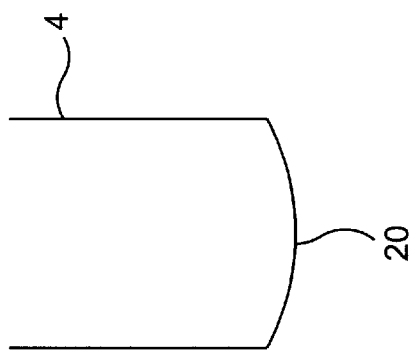
Figure 4D:
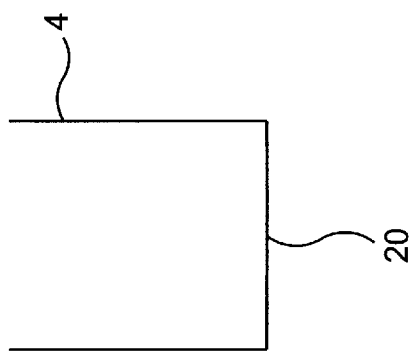

According to a possible embodiment the reflective surface 20 of the liquid storage chamber 4 is flat. Such an embodiment is shown in FIG. 4a. It is, however, also possible that the reflective surface 20 has such optical characteristics that the outgoing light beam 14 is collimated. This implies that it is also possible that the reflective surface of the storage chamber has such optical characteristics that the outgoing light beam is directed in a predetermined direction. In FIG. 4b such a possible embodiment of the reflective surface is shown. The surface 20, shown in FIG. 4b, has a concave form. Such a shape will result in the outgoing light beam 22 to be collimated in a predetermined direction. FIG. 4c shows an alternative storage chamber 4 having a flat bottom wall 20 with fresnel rings, wherein said fresnel rings form at least a portion of the reflective surface. Also the fresnel rings form a light focusing mirror with a focal length, matching the optical system and aiding light focusing on the light detector 14. Another suitable shape of the bottom wall of the storage chamber, is a flat bottom wall with an arrangement of cube corner prisms as shown in FIG. 4d. A regular pattern of reflecting cube corner prisms facing upwards could have special advantages, since its auto-collimating properties would ease the adjustment of the light detector considerably.

Since in the present invention the optical properties of the material of the liquid storage chamber are irrelevant, many different types of polymer can be used. The special form of the bottom can easily be produced in conventional manufacturing processes, like injection moulding that can be applied to polymers. Reflective coatings applicable to polymer surfaces for the embodiment, shown for example in FIGS. 4a and 4b, are well-known in the art and can easily and economically be applied by vapor deposition in high vacuum or more preferably by (electro)plating processes. Coatings of nickel, chrome, silver and other metals can such be applied to a variety of polymers.

Figure 5:
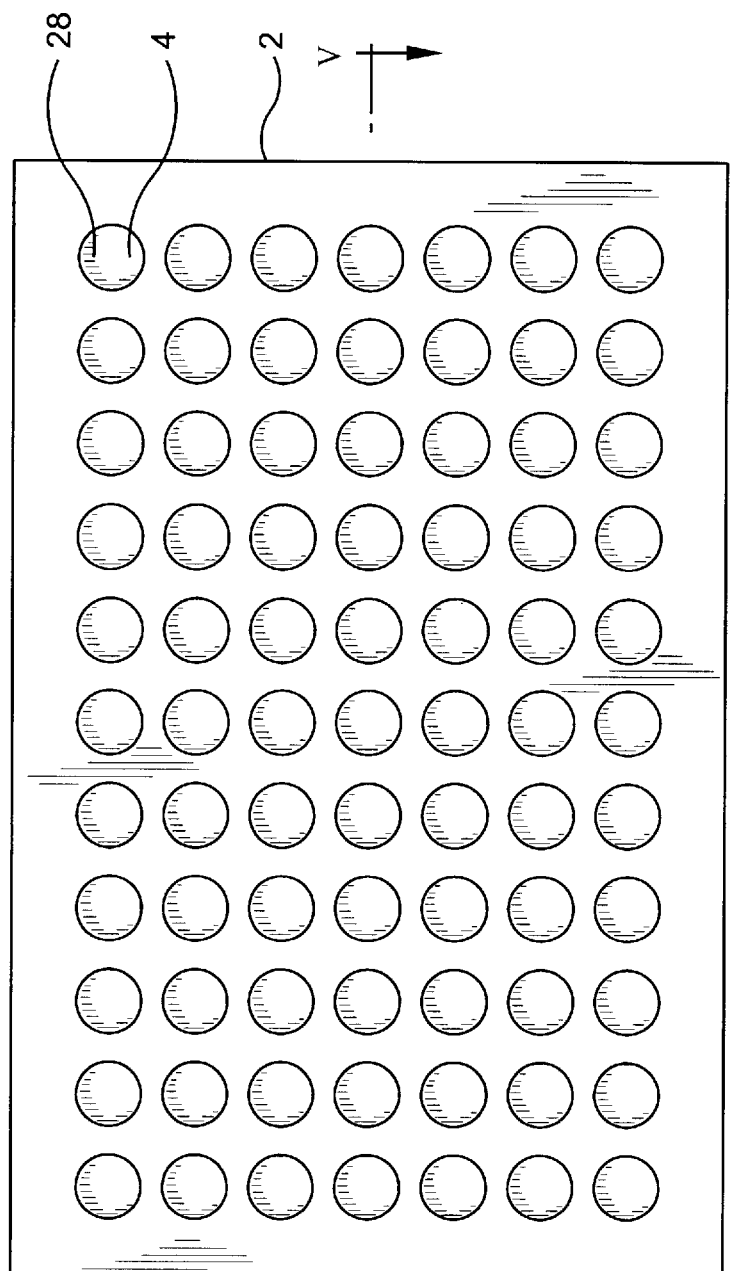
FIG. 5 shows a top view of a third embodiment of a photometric measuring system in accordance with the invention.
Figure 6:
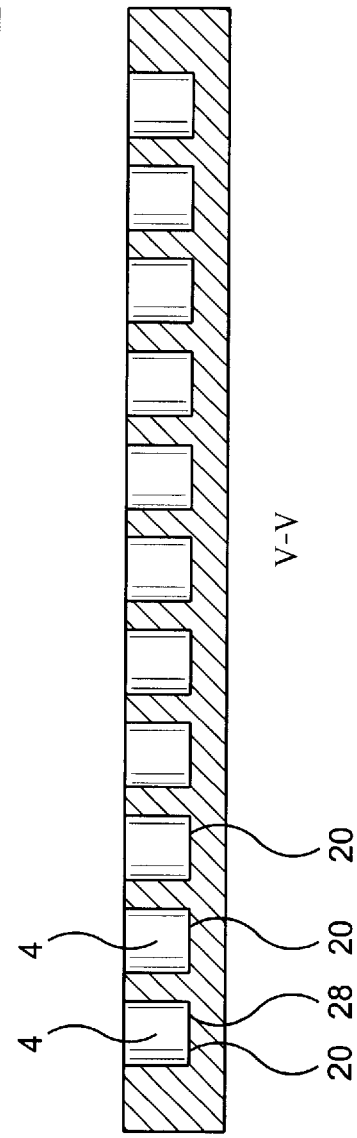
FIG. 6 shows a cross-section of the system of FIG. 5.
Figure 7:
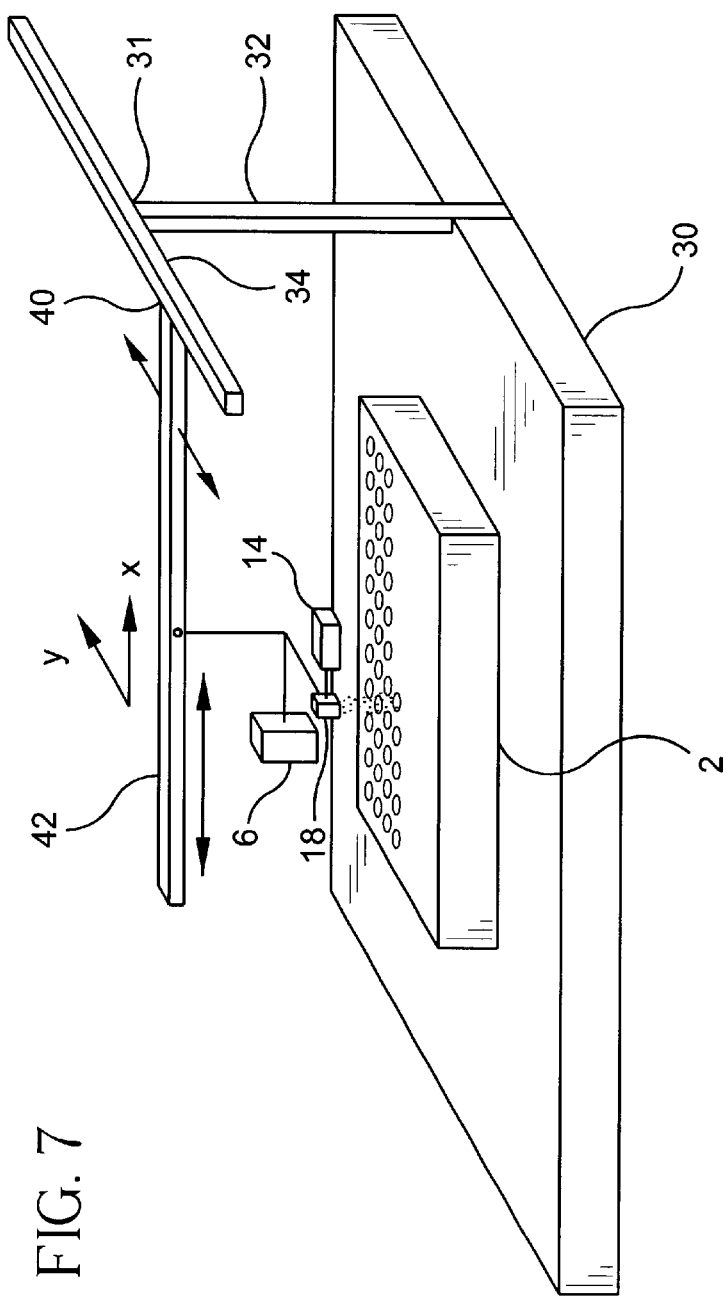
FIG. 7 shows a fourth embodiment of a photometric measuring system according to the invention.

According to a special embodiment as shown in FIGS. 5 and 6 the holder 2 is provided with a base plate 26, incorporating a number of holes 28. Each hole 28 forms a liquid storage chamber 4. In the present example the holder is provided with a plurality of storage chambers arranged in a matrix. Preferably, as shown in FIG. 7, the system is further provided with means for moving the holder incorporating such a plurality of storage chambers 4, relative to the light generator 6 and the light detector 14. In particular the system according to FIG. 7 is provided with a base plate 30 on top of which the holder 2 is positioned. An upstanding arm 32 is fixed to the base plate 30. A second arm 34 is connected to the top end of the vertical arm 32. The second arm 34 is directed parallel to the base plate 30. Finally a third arm 38 is movably connected to the second arm 34. The third arm 38 is directed perpendicular to the second arm 34 and parallel to the base plate 30. The system is provided with a motor connected to the second arm 34 and the third arm 38, respectively, for moving the third arm 38 in a plane which is parallel to the base plate 30, in a direction which is parallel to the longitudinal direction of the second arm 34. The light generator 6, the beam splitter 18 and the light detector 14 as shown in FIG. 2 are movably connected to the third arm 38. Motor means 42 are provided to move the combination of light generator 6, beam splitter 18 and the light detector 14 in a direction which is parallel to the longitudinal direction of the third arm 38. Hence, the combination of the light generator 6, beam splitter 18 and the light detector 14 can be moved in a plane, which is parallel to the base plate so as to enable successively measuring the liquids, present in the plurality of storage chambers 4 of the holder 2.

Figure 8:
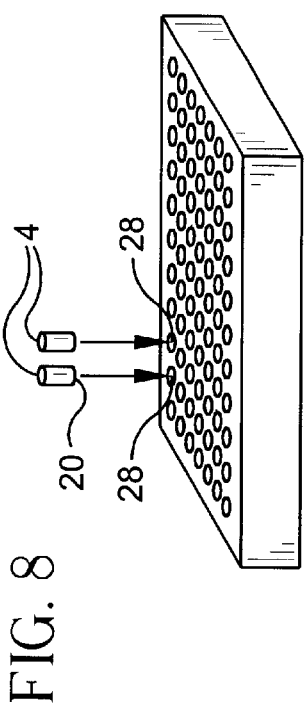
FIG. 8 shows a fifth embodiment of a photometric measuring system according to the invention.

FIG. 8 shows a special embodiment of the holder shown in FIGS. 5–7. According to this special embodiment the holder 2 is provided with the base plate 30, whereby the base plate incorporates a plurality of holes. However, the holes itself do not form the storage chambers. Instead the storage chambers 4 are removably positioned in the holes 28. The storage chambers 4 are provided with a reflective surface of the type discussed in accordance with the previous drawings.

It is noted that the invention is not limited to the embodiments shown in FIGS. 1–8. For example, the light generator 6 and the light detector 14 may be but need not be positioned on the same side of the storage chamber. Hence, it would also be possible by using a suitable arrangement of mirrors and/or lenses and/or prisms and/or fiberoptic light guides to position the light generator 6 and/or the light detector 14 on any desired location relative to the storage chamber 4. Such variations and other obvious variations are all considered to fall within the scope of the present invention.

What is claimed is:

1. A photometric measuring system, comprising a holder (2) provided with at least one storage chamber (4) for holding a fluid to be measured, at least light generator (6) for generating a light beam (8) to interact with the fluid in the storage chamber (4) and at least one light detector (14) for detecting, during operation, at least a portion of the light which has interacted with the fluid present in the storage chamber (4), in which system at least a portion of the walls of the storage chamber (4) has been provided with a reflective surface (20) so that at least a portion of the light which has entered the storage chamber (4) will be reflected and detected by the detector (14), characterized in that, in order to realize a photometric measurement which can be carried out with respect to the fluid in the storage chamber (4) independent of the wavelength of the generated light beam (8), each storage chamber (4) has an upper open end and the generator (6) as well as the detector (14) can be arranged at a predetermined distance above said upper open end, such that the light and the light path between the light generator (6) and the detector (14) does not meet any physical window.

2. A photometric measuring system according to claim 1, characterized in that the reflective surface (20) of a storage chamber (4) has such optical characteristics that the reflected light is collimated.

3. A photometric measuring system according to claim 1, characterized in that the reflective surface (20) of a storage chamber (4) has such optical characteristics, particularly such a shape, that the reflected light is directed in a predetermined direction.

4. A photometric measuring system according to claim 1, characterized in that the reflective surface (20) of the storage chamber (4) has a concave shape so that the reflected light is collimated (FIG. 4b).

5. A photometric measuring system according to claim 2, characterized in that the storage chamber (4) comprises a flat bottom wall with fresnel rings wherein said fresnel rings form at least a portion of the reflective surface (20) (FIG. 4c).

6. A photometric measuring system according to claim 2, characterized in that the storage chamber (4) comprises a flat bottom wall with an arrangement of cube prisms (FIG. 4d).

7. A photometric measuring system according to claim 1, characterized in that the holder (2) is provided with a bases plate (30) incorporating at least one hole (28) whereby the storage chamber (4) is removably positioned in said hole (28) (FIG. 8).

8. An array of storage chambers of the type as disclosed in claim 1, characterized in that the storage chambers are used in a matrix arrangement.

* * * * *

UNITED STATES PATENT AND TRADEMARK OFFICE
CERTIFICATE OF CORRECTION

PATENT NO. : 6,239,875 B1
DATED : May 29, 2001
INVENTOR(S) : Verheijen

It is certified that error appears in the above-identified patent and that said Letters Patent is hereby corrected as shown below:

<u>Title page,</u>
Item [86] § 371 Date, now read "May 13, 1999" should read -- May 13, 1998 --.
Item [86] § 102(e) Date, now read "May 13, 1999" should read -- May 13, 1998 --.

Signed and Sealed this

Ninth Day of April, 2002

Attest:

JAMES E. ROGAN
Attesting Officer
Director of the United States Patent and Trademark Office

UNITED STATES PATENT AND TRADEMARK OFFICE
CERTIFICATE OF CORRECTION

PATENT NO. : 6,239,875 B1
DATED : May 29, 2001
INVENTOR(S) : Verheijen

It is certified that error appears in the above-identified patent and that said Letters Patent is hereby corrected as shown below:

<u>Title page,</u>
Item [73], Assignee, now read -- Nederlandse Organisatie Voor Toegepast-Natuurwetenschappelijk, Delft (NL)" should read -- Nederlandse Organisatie Voor Toegepast-Natuurwetenschappelijk Onderzoek TNO, Delft (NL) --.

Signed and Sealed this

Sixteenth Day of July, 2002

*Attest:*

*Attesting Officer*

JAMES E. ROGAN
*Director of the United States Patent and Trademark Office*